(12) United States Patent
Zhang

(10) Patent No.: US 9,841,357 B2
(45) Date of Patent: Dec. 12, 2017

(54) SYSTEM FOR SENSING PARTICULATE MATTER

(71) Applicant: Ford Global Technologies, LLC, Dearborn, MI (US)

(72) Inventor: Xiaogang Zhang, Novi, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 95 days.

(21) Appl. No.: 14/966,408

(22) Filed: Dec. 11, 2015

(65) Prior Publication Data

US 2017/0167951 A1 Jun. 15, 2017

(51) Int. Cl.
*G01M 15/00* (2006.01)
*G01M 15/10* (2006.01)
*G01N 27/04* (2006.01)

(52) U.S. Cl.
CPC .......... *G01M 15/102* (2013.01); *G01N 27/04* (2013.01)

(58) Field of Classification Search
USPC ........................................ 73/114.71, 114.69
See application file for complete search history.

(56) References Cited

U.S. PATENT DOCUMENTS

| | | | | |
|---|---|---|---|---|
| 2,738,431 | A | * | 3/1956 | Herzog .................. H01J 47/08 250/386 |
| 6,517,612 | B1 | * | 2/2003 | Crouch ................ B01D 33/067 55/304 |
| 8,225,548 | B2 | | 7/2012 | McProud et al. |
| 8,310,249 | B2 | * | 11/2012 | Paterson ............. F02D 41/1466 324/693 |
| 2008/0011052 | A1 | | 1/2008 | Kondo et al. |
| 2009/0301058 | A1 | * | 12/2009 | Boehler ............. G01N 15/0656 60/276 |
| 2015/0253233 | A1 | | 9/2015 | Brueck et al. |
| 2015/0355067 | A1 | * | 12/2015 | Zhang ................ G01N 15/0656 73/23.31 |
| 2016/0131013 | A1 | * | 5/2016 | Yi .......................... F01N 13/08 60/274 |

FOREIGN PATENT DOCUMENTS

| | | |
|---|---|---|
| DE | 102004043122 A1 | 3/2006 |
| DE | 102006002111 A1 | 8/2006 |
| WO | 2006027287 A1 | 3/2006 |

OTHER PUBLICATIONS

Zhang, Xiaogang, "Method and System for Exhaust Particulate Matter Sensing," U.S. Appl. No. 14/835,270, filed Aug. 25, 2015, 50 pages.
Bilby, David, "Method and System for Exhaust Particulate Matter Sensing," U.S. Appl. No. 14/937,632, filed Nov. 10, 2015, 48 pages.

* cited by examiner

*Primary Examiner* — Clayton E Laballe
*Assistant Examiner* — Warren K Fenwick
(74) *Attorney, Agent, or Firm* — Julia Voutyras; McCoy Russell LLP

(57) ABSTRACT

Methods and systems are provided for sensing particulate matter in an exhaust system of a vehicle. An example system comprises a particulate matter sensor inside a tube configured to receive a portion of exhaust gas in an exhaust passage.

20 Claims, 5 Drawing Sheets

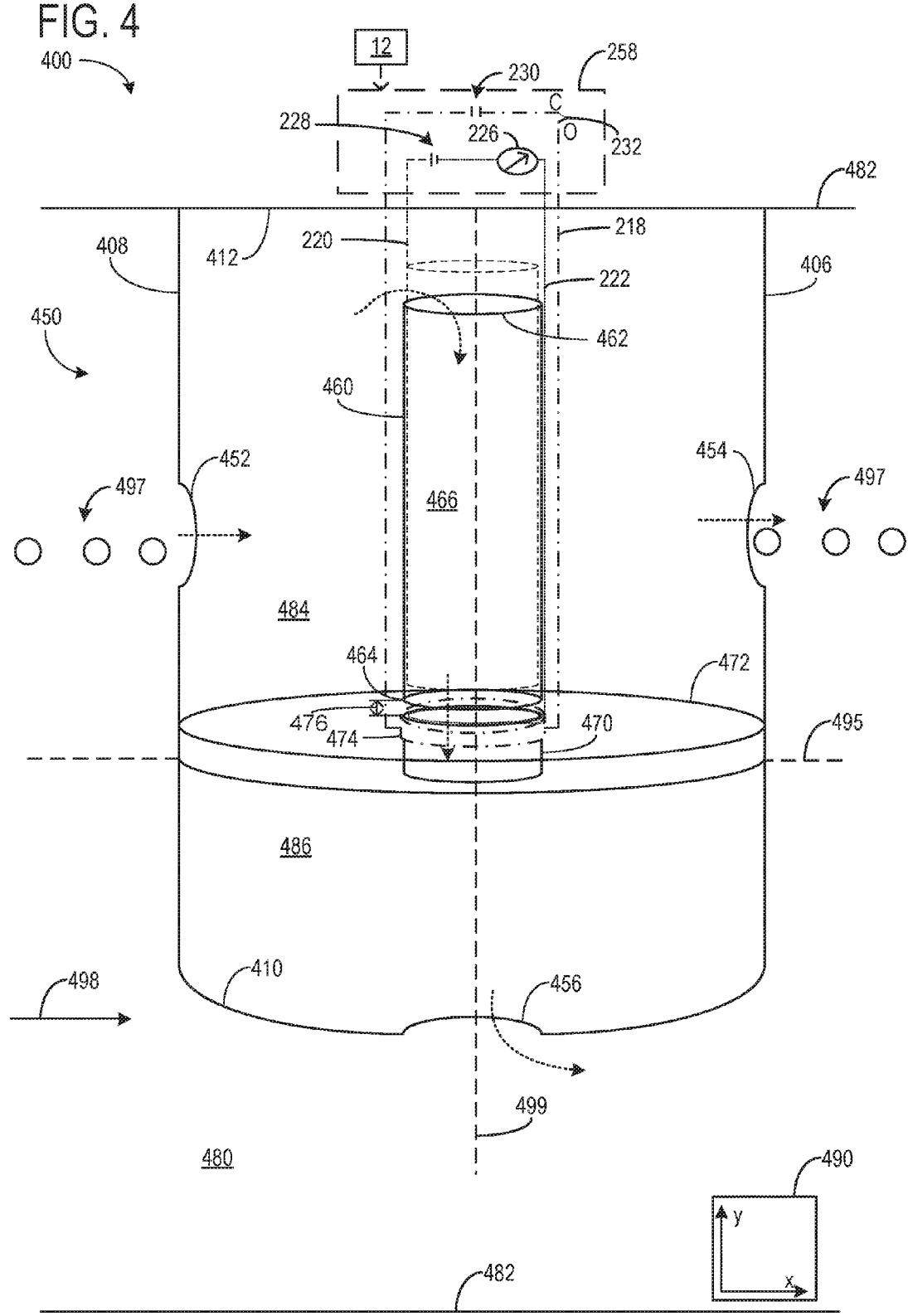

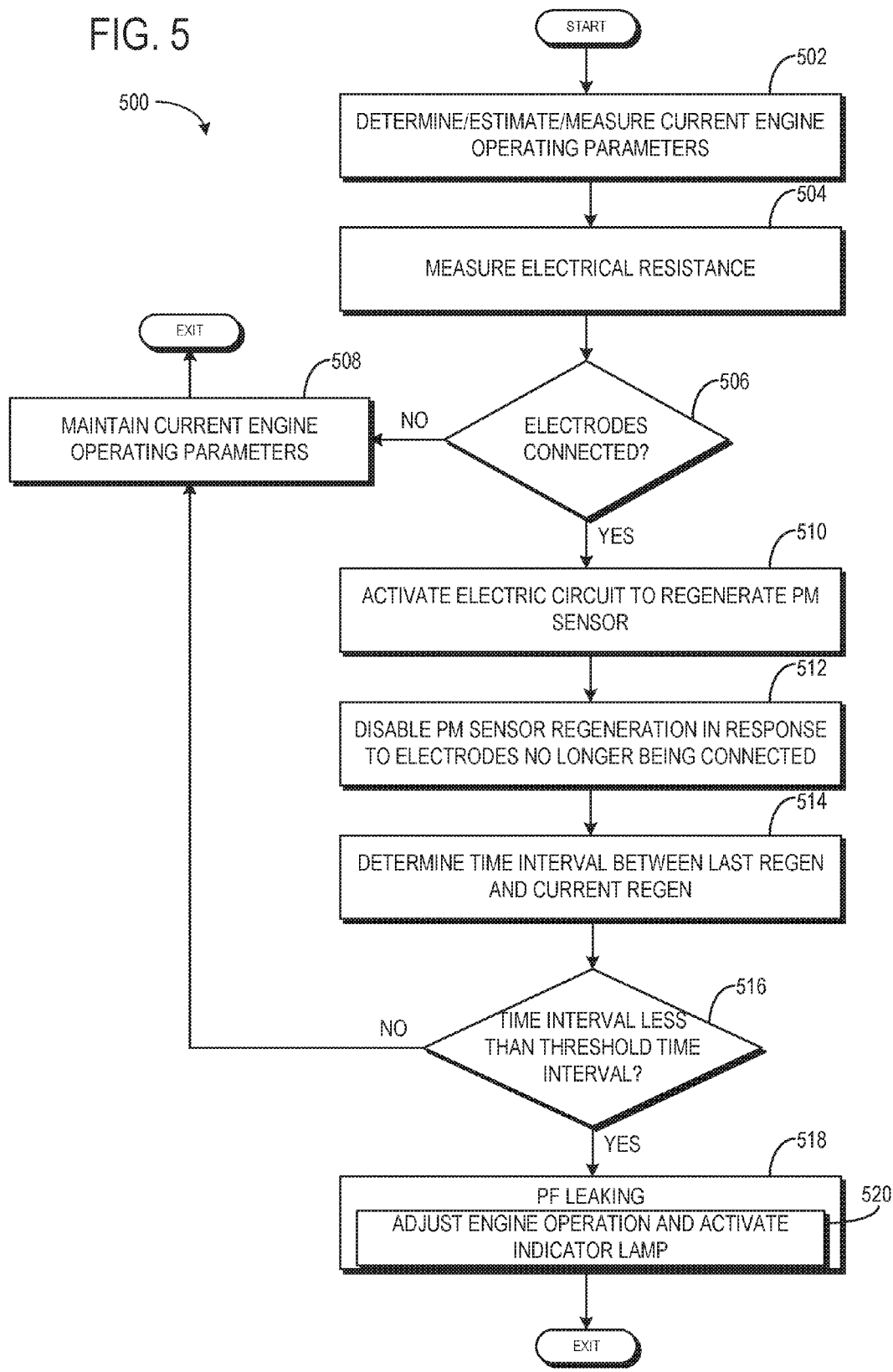

SYSTEM FOR SENSING PARTICULATE MATTER

FIELD

The present description relates generally to methods and systems for sensing particulate matter in an exhaust system.

BACKGROUND/SUMMARY

Engine emission control systems may utilize various exhaust sensors. One example sensor may be a particulate matter sensor which indicates particulate matter mass and/or concentration in the exhaust gas. In one example, the particulate matter sensor may operate by accumulating particulate matter over time and providing an indication of the degree of accumulation as a measure of exhaust particulate matter levels.

Particulate matter sensors may correlate a measured change in electrical conductivity (or resistivity) between a pair of electrodes placed on a substrate surface of the sensor with the amount of particulate matter deposited between the electrodes. Particulate matter sensors may encounter problems with non-uniform deposition of soot on the sensor surface due to a bias in flow distribution across the surface of the sensor. Further, particulate matter sensors may be prone to contamination from an impingement of water droplets and/or larger particulates present in the exhaust gases. This contamination may lead to errors in sensor output.

Other attempts to address particulate matter sensor deposition include shielding the sensor with a tube. One example approach is shown by Nelson et al. in U.S. Pat. No. 8,225,548. Therein, a PM sensor includes a flow redirector and a barrier positioned around a PM sensor element to filter out the larger particulates from impinging the PM sensor element. The barrier thus serves to block larger particulates in the exhaust flow from impinging on the PM sensor element, thereby reducing PM sensor sensitivity fluctuations due to large particulates depositing on the PM sensor element.

However, the inventors herein have recognized potential issues with systems such as Nelson. As one example, planar substrate surfaces may be susceptible to uneven particulate matter (PM) deposition due to the surface receiving exhaust gas from a small portion of the sensor device. Furthermore, an opening of the sensor tube faces an upstream direction relative to a direction of exhaust gas flow. This allows large particulates to readily flow into the sensor tube, which may inadvertently accumulate onto the sensor despite a design of the sensor tube.

The inventors herein have recognized the above issues and identified an approach to at least partly address both the general issues as well as particular issues with Nelson. In one example, the issues described above may be addressed by a system comprising a plurality of hollow discs increasing in diameter along a vertical axis, a first electrode installed on surfaces of each alternating disc of the plurality of discs, a second electrode installed on surfaces of each remaining disc of the plurality of discs, and a tube with an inlet facing a downstream direction relative to engine exhaust flow. In this way, large particulates may not enter the tube due to their momentum while the discs capture particulate matter from a greater range of the tube compared to the prior art.

As one example, the discs may increase in size with respect to a direction of exhaust flow in the tube. An outer rim (edge) of larger discs may extend beyond an outer circumference of smaller discs, where the edges face a direction of exhaust flow in the tube. Particulate matter (PM) may deposit on the edges and bridge the first and second electrodes after exceeding a threshold PM load. Large particulates and/or water droplets may not flow through the tube due to the configuration of the tube opening and a greater momentum of large particulate/water droplets compared to smaller PM. Overall, functioning of the PM sensor may be improved and may be more reliable.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIG. 4 shows a third exemplary embodiment of a PM sensor assembly.

FIGS. 2-4 are shown approximately to scale, although other relative dimensions may be used.

FIG. 5 shows a method for determining if a particulate filter demands a regeneration or is degraded.

DETAILED DESCRIPTION

Figure 1:
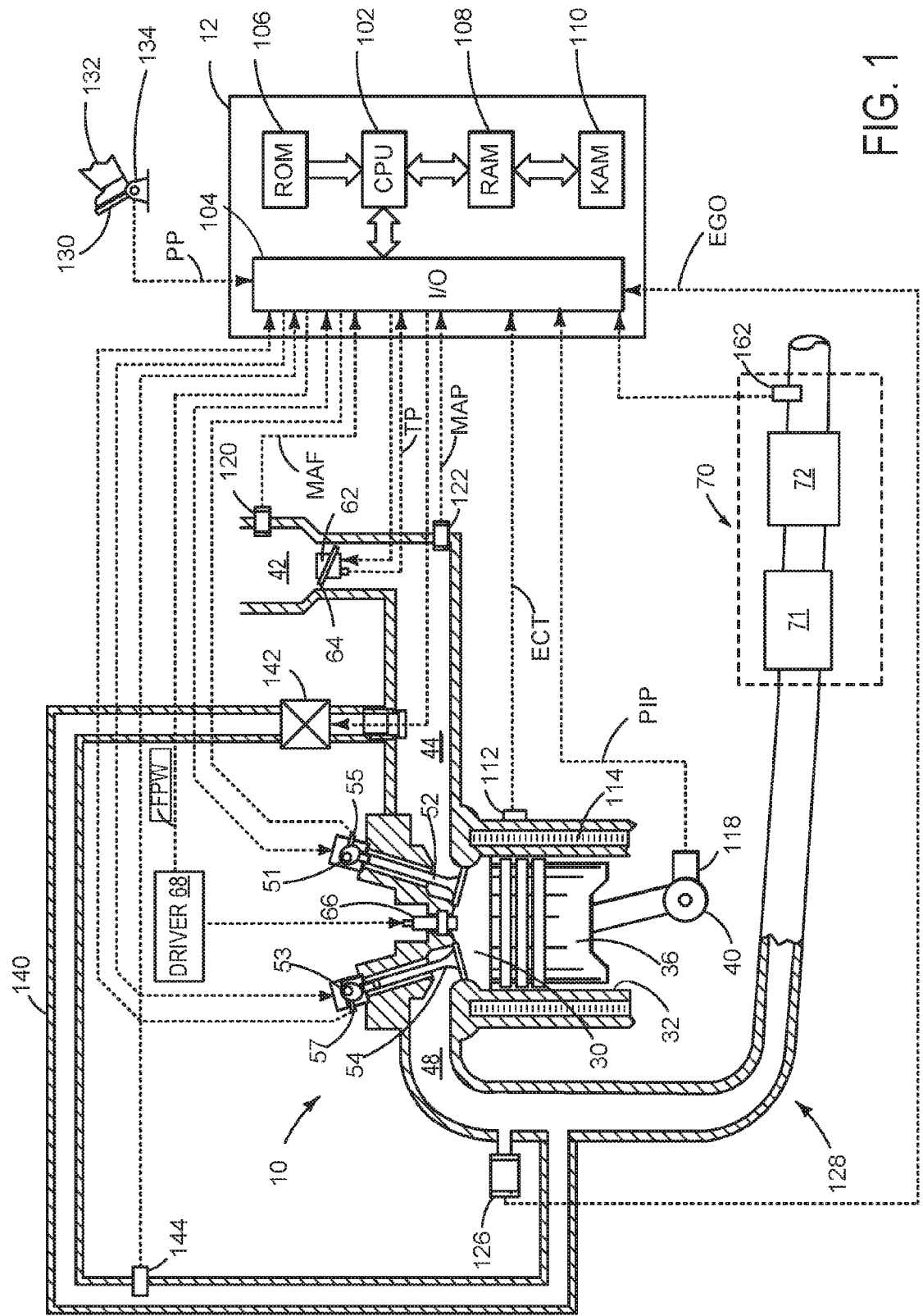
FIG. 1 is a schematic diagram of an engine.
Figure 2:
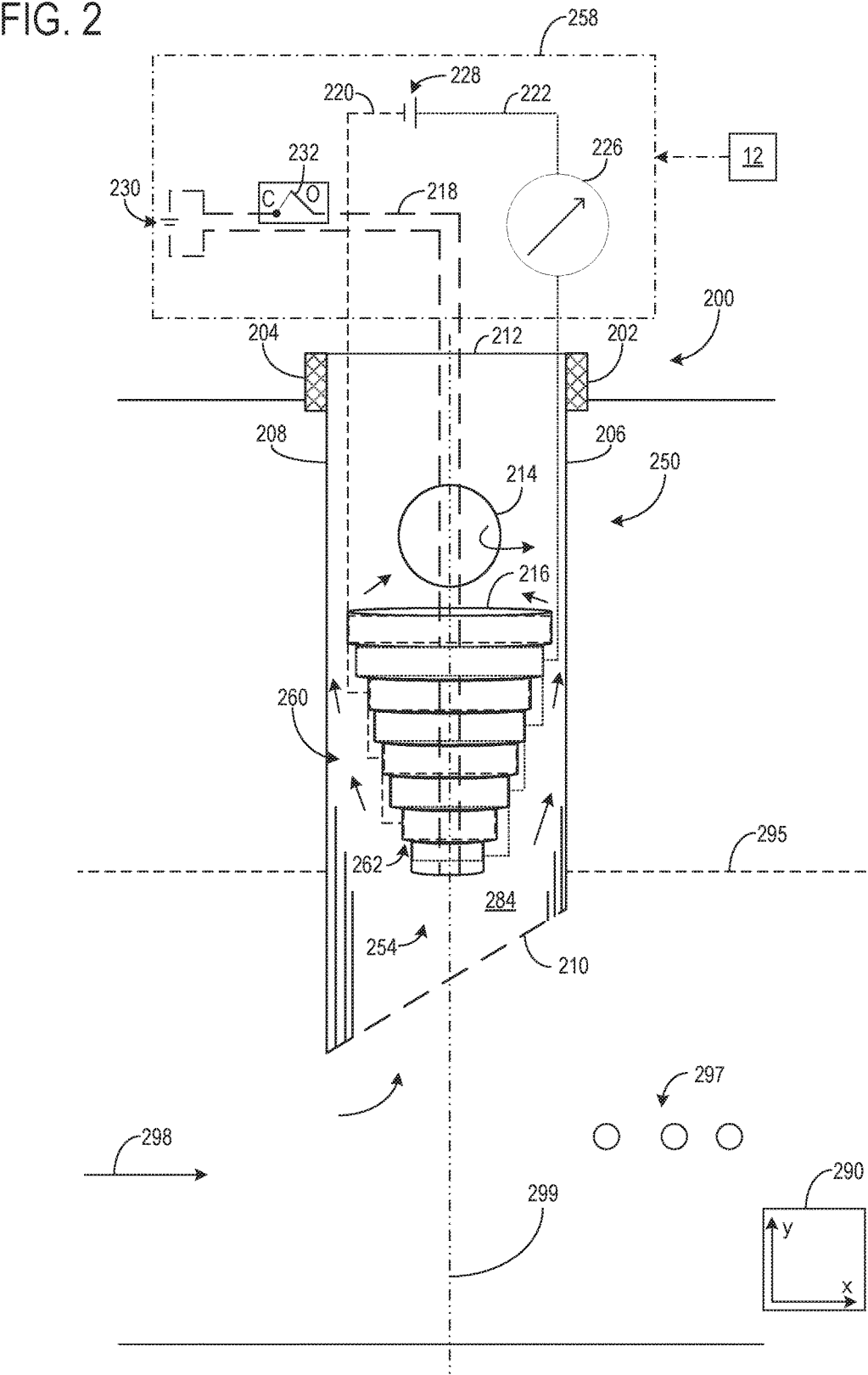
FIG. 2 shows a first exemplary embodiment of a particulate matter (PM) sensor assembly.
Figure 3:
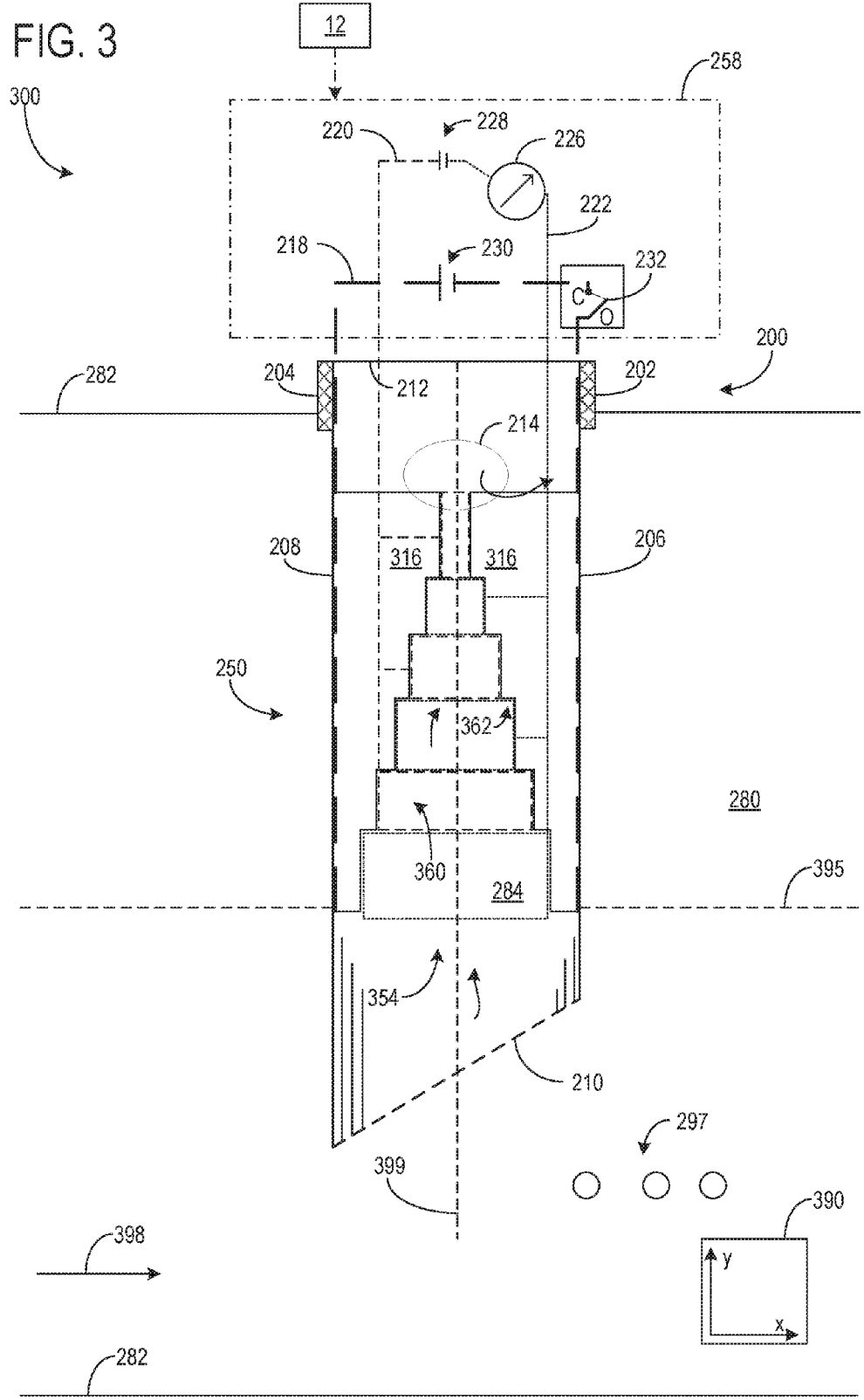
FIG. 3 shows a second exemplary embodiment of a PM sensor assembly.

The following description relates to a particulate matter (PM) sensor assembly. The PM sensor assembly may include a tube serving as a barrier for a PM sensor, which may prevent large particulate and/or water droplets from flowing to the PM sensor. The PM sensor assembly may be located downstream of a particulate filter in an exhaust passage of an engine as shown in FIG. 1. The PM sensor assembly may capture soot via a plurality of stacked discs, where the discs increase in diameter along a direction of exhaust flow in the sensor assembly. Edges of larger discs may extend beyond edges of smaller discs creating a surface between electrodes where soot may be captured. As soot accumulates, electrodes of the PM sensor assembly may become bridged, indicating one or more of a particulate filter in an exhaust passage being fully loaded and/or degraded. Examples of the PM sensor assembly are shown in FIGS. 2, 3, and 4. A method for determining if the particulate filter in the exhaust passage is fully loaded and/or degraded is shown in FIG. 5.

FIGS. 1-4 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example.

Referring now to FIG. 1, it shows a schematic diagram with one cylinder of multi-cylinder engine 10, which may be included in a propulsion system of a vehicle. Engine 10 may be controlled at least partially by a control system including a controller 12 and by input from a vehicle operator 132 via an input device 130. In this example, input device 130 includes an accelerator pedal and a pedal position sensor 134 for generating a proportional pedal position signal PP. A combustion chamber 30 (also termed, cylinder 30) of the engine 10 may include combustion chamber walls 32 with a piston 36 positioned therein. Piston 36 may be coupled to a crankshaft 40 so that reciprocating motion of the piston is translated into rotational motion of the crankshaft 40. Crankshaft 40 may be coupled to at least one drive wheel (not shown) of a vehicle via an intermediate transmission system (not shown). Further, a starter motor (not shown) may be coupled to the crankshaft 40 via a flywheel (not shown) to enable a starting operation of the engine 10.

Combustion chamber 30 may receive intake air from an intake manifold 44 via an intake passage 42 and may exhaust combustion gases via an exhaust passage 48. The intake manifold 44 and the exhaust passage 48 can selectively communicate with the combustion chamber 30 via intake valve 52 and exhaust valve 54 respectively. In some embodiments, the combustion chamber 30 may include two or more intake valves and/or two or more exhaust valves.

In the example depicted in FIG. 1, the intake valve 52 and exhaust valve 54 may be controlled by cam actuation via respective cam actuation systems 51 and 53. The cam actuation systems 51 and 53 may each include one or more cams and may utilize one or more of cam profile switching (CPS), variable cam timing (VCT), variable valve timing (VVT), and/or variable valve lift (VVL) systems that may be operated by the controller 12 to vary valve operation. The position of the intake valve 52 and the exhaust valve 54 may be determined by position sensors 55 and 57, respectively. In alternative embodiments, the intake valve 52 and/or exhaust valve 54 may be controlled by electric valve actuation. For example, the cylinder 30 may alternatively include an intake valve controlled via electric valve actuation and an exhaust valve controlled via cam actuation including CPS and/or VCT systems.

In some embodiments, each cylinder of the engine 10 may be configured with one or more fuel injectors for providing fuel thereto. As a non-limiting example, the cylinder 30 is shown including one fuel injector 66. Fuel injector 66 is shown coupled to the cylinder 30 for injecting fuel directly therein in proportion to the pulse width of signal FPW received from controller 12 via electronic driver 68. In this manner, fuel injector 66 provides what is known as direct injection of fuel into combustion chamber 30. It will also be appreciated that the cylinder 30 may receive fuel from a plurality of injections during a combustion cycle. In other examples, the fuel injector may be mounted in the side of the combustion chamber or in the top of the combustion chamber, for example. Fuel may be delivered to fuel injector 66 by a fuel system (not shown) including a fuel tank, a fuel pump, and a fuel rail.

In the example shown in FIG. 1, engine 10 is configured as a diesel engine that combusts air and diesel fuel through compression ignition. In other embodiments, the engine 10 may combust a different fuel including gasoline, biodiesel, or an alcohol containing fuel blend (e.g., gasoline and ethanol, or gasoline and methanol) through compression ignition and/or spark ignition. Thus, the embodiments described herein may be used in any suitable engine, including but not limited to, diesel and gasoline compression ignition engines, spark ignition engines, direct or port injection engines, etc.

The intake passage 42 may include a throttle 62 having a throttle disc 64. In this particular example, the position of the throttle disc 64 may be varied by controller 12 via a signal provided to an electric motor or actuator included with the throttle 62, a configuration that is commonly referred to as electronic throttle control (ETC). In this manner, the throttle 62 may be operated to vary the intake air provided to the combustion chamber 30 among other engine cylinders. The position of the throttle disc 64 may be provided to the controller 12 by throttle position signal TP. The intake passage 42 may include a mass air flow sensor 120 and a manifold air pressure sensor 122 for providing respective signals MAF and MAP to the controller 12.

Further, in the disclosed embodiments, an exhaust gas recirculation (EGR) system may route a desired portion of exhaust gas from the exhaust passage 48 to the intake manifold 44 via an EGR passage 140. An amount of EGR provided may be varied by controller 12 via an EGR valve 142. By introducing exhaust gas to the engine 10, the amount of available oxygen for combustion is decreased, thereby reducing combustion flame temperatures and reducing the formation of NOx, for example. As depicted, the EGR system further includes an EGR sensor 144 which may be arranged within the EGR passage 140 and may provide an indication of one or more of pressure, temperature, and concentration of the exhaust gas. Under some conditions, the EGR system may be used to regulate the temperature of the air and fuel mixture within the combustion chamber 30, thus providing a method of controlling the timing of ignition during some combustion modes. Further, during some conditions, a portion of combustion gases may be retained or trapped in the combustion chamber by controlling exhaust valve timing, such as by controlling a variable valve timing mechanism.

An exhaust system 128 includes an exhaust gas sensor 126 coupled to the exhaust passage 48 upstream of an emission control system 70 and the EGR passage 140. Exhaust gas sensor 126 may be any suitable sensor for providing an indication of exhaust gas air/fuel ratio such as a linear oxygen sensor or UEGO (universal or wide-range exhaust gas oxygen), a two-state oxygen sensor or EGO, a HEGO (heated EGO), NOx, HC, or CO sensor.

Emission control system 70 is shown arranged along exhaust passage 48 downstream of exhaust gas sensor 126. Emission control system 70 may be a selective catalytic reduction (SCR) system, three way catalyst (TWC), NOx trap, various other emission control devices, or combinations thereof. For example, emission control system 70 may include an SCR catalyst 71 and a particulate filter (PF) 72. In some embodiments, PF 72 may be located downstream of the SCR catalyst 71 (as shown in FIG. 1), while in other embodiments, PF 72 may be positioned upstream of the SCR catalyst 71 (not shown in FIG. 1). Emission control system 70 may further include exhaust gas sensor 162. Sensor 162 may be any suitable sensor for providing an indication of a concentration of exhaust gas constituents such as a NOx, NH3, EGO, or a particulate matter (PM) sensor, for example. In some embodiments sensor 162 may be located downstream of PF 72 (as shown in FIG. 1), while in other embodiments, sensor 162 may be positioned upstream of PF 72 (not shown in FIG. 1). Further, it will be appreciated that more than one sensor 162 may be provided along the exhaust passage 48.

As described in more detail with reference to FIG. 2, sensor 162 may be a PM sensor assembly comprising a PM sensor and may measure the mass or concentration of particulate matter downstream of PF 72. For example, sensor 162 may be a soot sensor. Sensor 162 may be operatively coupled to controller 12 and may communicate with controller 12 to indicate a concentration of particulate matter within exhaust exiting PF 72 and flowing through exhaust passage 48. In this way, sensor 162 may detect leakages from PF 72.

Further, in some embodiments, during operation of engine 10, emission control system 70 may be periodically reset by operating at least one cylinder of the engine within a particular air/fuel ratio.

Controller 12 is shown in FIG. 1 as a microcomputer, including a microprocessor unit 102, input/output ports 104, an electronic storage medium for executable programs and calibration values shown as a read only memory chip 106 in this particular example, random access memory 108, keep alive memory 110, and a data bus. The controller 12 may be in communication with and, therefore, receive various signals from sensors coupled to the engine 10, in addition to those signals previously discussed, including measurement of inducted mass air flow (MAF) from the mass air flow sensor 120; engine coolant temperature (ECT) from a temperature sensor 112 coupled to a cooling sleeve 114; a profile ignition pickup signal (PIP) from a Hall effect sensor 118 (or other type) coupled to the crankshaft 40; throttle position (TP) from a throttle position sensor; absolute manifold pressure signal, MAP, from the sensor 122; and exhaust constituent concentration from the exhaust gas sensor 126. Engine speed signal, RPM, may be generated by controller 12 from signal PIP.

The controller 12 receives signals from the various sensors of FIG. 1 (e.g., exhaust gas sensor 162) and employs the various actuators of FIG. 1 to adjust engine operation based on the received signals and instructions stored on a memory of the controller.

As described above, FIG. 1 shows only one cylinder of a multi-cylinder engine, and each cylinder may similarly include its own set of intake/exhaust valves, fuel injector(s), spark plug(s), etc.

FIG. 2 shows a schematic view of a first embodiment of a particulate matter (PM) sensor assembly 200. The PM sensor assembly 200 may be used similarly to or with sensor 162 in the embodiment of FIG. 1 and therefore may share common features and/or configurations as those already described for exhaust gas sensor 162. The PM sensor assembly 200 may be configured to measure PM mass and/or concentration in the exhaust gas of an exhaust passage 280. The PM sensor assembly 200 comprises a protection tube 250 that may shield a PM sensor element 254 of the PM sensor assembly 200 while additionally redirecting exhaust flow as described below. It will be appreciated that PM sensor assembly 200 is shown in simplified form by way of example and that other configurations are possible.

An axis system 290 includes two axes, an x-axis parallel to the horizontal axis and a y-axis parallel to the vertical axis. A central axis 295 of the exhaust passage 280 is parallel to the x-axis. A sensor central axis 299 is parallel to the y-axis (perpendicular to the central axis 295). Arrow 298 depicts a general direction of incoming exhaust gas flow. Arrows indicate a general flow of exhaust in the PM sensor 200.

The PM sensor element 254 includes a first electrode 220 (depicted by a medium dash line) and a second electrode 222 (depicted by a small dash line) spaced away from each other around the PM sensor element 254. Medium dashes are larger than small dashes. The electrodes are oppositely charged, wherein the first electrode 220 is positively charged and the second electrode 222 is negatively charged. Alternatively, the first electrode 220 may be negatively charged and the second electrode 222 may be positively charged. These electrodes may be typically manufactured from metals such as platinum, gold, osmium, rhodium, iridium, ruthenium, aluminum, titanium, zirconium, and the like, as well as, oxides, cements, alloys and combination comprising at least one of the foregoing metals. The electrodes are formed on a sensor substrate 216 that is typically manufactured from highly electrically insulating materials. Possible electrically insulating materials may include oxides such as alumina, zirconia, yttria, lanthanum oxide, silica, and combinations comprising at least one of the foregoing, or any like material capable of inhibiting electrical communication and providing physical protection for the pair of interdigitated electrodes. Spacing between the two electrodes may be in a range from 10 micrometers to 100 micrometers along features of the sensor substrate 216 with a line width of each electrode being about the same value.

The first electrode 220 is connected to a positive terminal of a voltage source 228 of an electric circuit 258. The second electrode 222 is connected to a measurement device 226, which may produce a sensor output, and to a negative terminal of the voltage source 228. The sensor output may be indicative of particulate matter in the engine exhaust gas flow. The electric circuit 258, the voltage source 228, and the measurement device 226 are located away from the exhaust passage 280 by some distance (e.g., less than one meter). Further, the voltage source 228 and the measurement device 226 of the electric circuit 258 may be controlled by a controller, such as controller 12 of FIG. 1, so that particulate matter collected at the PM sensor may be used for diagnosing leaks in a particulate filter (PF) of the exhaust passage 280 (e.g., particulate filter 70 of exhaust passage 48), for example. As such, the measurement device 226 may be any device capable of reading a resistance change across the electrodes, such as a voltmeter. The electrodes may bridge as PM is deposited onto the sensor substrate 216 between the electrodes, as will be described below. A resistance between the electrodes may start to decrease once a deposition of PM spans an entire distance between the electrodes (the electrodes are bridged), which is indicated by a decrease in the voltage measured by the measurement device 226. The controller 12 may be able to determine the resistance between the electrodes as a function of voltage measured by the measurement device 226 and infer a corresponding PM or soot load on the PM sensor element 254. A functioning and/or state of the PF may be determined by monitoring the PM load on the PM sensor element 254.

The PM sensor element 254 also includes a heating element 218 that is be integrated into the sensor substrate 216. In alternate embodiments, the PM sensor element 254 may not include a heating element 218. The heating element 218 traverses along the sensor central axis 299 through a body of the sensor substrate 216. The heating element 218 may comprise, but is not limited to, a temperature sensor, and a heater. Possible materials for the heater and the temperature sensor forming the heating element 218 may include platinum, gold, palladium, and the like; and alloys, oxides, and combinations comprising at least one of the foregoing materials, with platinum/alumina, platinum/palladium, platinum, and palladium. The heating element 218 may be used for regenerating the sensor substrate 216. Specifically, during conditions when the particulate matter load or soot load of the sensor substrate 216 is higher than a threshold load (indicated by a decrease in resistance of one or more of the electrodes), heating element 218 may be operated to burn accumulated soot particles from the sensor substrate 216 by increasing a sensor substrate temperature. During PM sensor regeneration, the controller 12 may provide a voltage to a voltage source 230. In addition, the controller may close the switch 232 (moves to the C-position) for a threshold time to apply the voltage via the voltage source 230 to the heating element 218 in order to raise the temperature of the heating element 218. Subsequently, when the sensor electrodes are sufficiently clean, the controller may open the switch 232 (moves to the O-position) to stop heating the heating element 218 as shown. By intermittently regenerating the PM sensor 200, it may be returned to a condition (e.g., unloaded or only partially loaded condition) more suitable for collecting exhaust soot. In addition, accurate information pertaining to the exhaust soot level may be inferred from the sensor regeneration and this information may be used by the controller for diagnosing leaks in the particulate filter. This information may be muddled by larger particulates and water droplets impinging onto the sensor substrate 216.

A protection tube 250, housing PM sensor element 254, may be a hollow cylindrical tube with an upstream tube wall 208 (upstream facing wall), a downstream tube wall 206 (downstream facing wall), and a top surface 212. The upstream tube wall 208 may be closer to a PF than the downstream tube wall 206 when positioned in an exhaust passage 280 (such as PF 72 in the exhaust passage 48 shown in FIG. 1). Further, exhaust gases flowing through the exhaust passage 280 may first contact the upstream tube wall 208. The top surface 212 may further include geometrical openings through which the PM sensor element 254 and its accompanying electrical connections may be inserted through into the protection tube 250. Furthermore, exhaust gas may not flow through the top surface 212. The protection tube 250 may be mounted onto an engine exhaust pipe 282 of the exhaust passage 280 via sensor bosses 202 and 204 such that the protection tube 250 aligns with and is parallel to the sensor central axis 299. The protection tube 250 and the exhaust pipe 282 are hermetically sealed to each other and prevent exhaust gas from flowing to an engine or an ambient atmosphere. The protection tube 250 is mounted on a highest point of the exhaust pipe 282 for a vehicle on a flat surface. In one example, there may be a single, circular sensor boss spanning an entire circumference of the protection tube 250, mounting the protection tube 250 onto the exhaust pipe 282. As shown, the protection tube 250 extends through an entire thickness of the exhaust pipe 282 and into a portion of the exhaust passage 280. The depth to which the protection tube 250 extends into the exhaust passage 280 may depend on a diameter of the exhaust pipe 282. In some examples, the protection tube 250 may extend to about one-third to two-thirds of the exhaust pipe diameter. Other depths may be realized.

A bottom of the protection tube 250 may be cut at an angle (dashed line 210) forming an angled inlet that introduces exhaust flow into the PM sensor assembly 200. The angled bottom portion (210) may be a 30° or 45° angle with respect to the x-axis (central axis 295). As such, the length of the upstream tube wall 208 is larger than the length of the downstream tube wall 206. Thus, the angled bottom opening 210 faces a downstream direction away from incoming exhaust flow. Larger particulates and water droplets may flow past the angled opening 210 due to their greater momentum compared to smaller particulates, which may enter the angled opening (herein referred to as inlet) 210. The PM sensor assembly 200 further includes an outlet 214 positioned away from the inlet 210, above a sensor substrate 216, and adjacent to the top surface 212. The outlet 214 may be a single hole or a plurality of holes positioned along a back wall or front wall of the protection tube, facing a direction perpendicular to exhaust flow in the exhaust passage 280. The back and front walls are different than the upstream 208 and downstream 206 surfaces. The back, front, upstream, 208, and downstream 206 walls are contiguous, curved walls coupled to a circumference of the top surface 212. While the outlet 214 is shown as an elliptical hole, other shapes and sizes of the outlet 214 may also be used without departing from the scope of this disclosure.

The sensor substrate 216 comprises a plurality of concentrically stacked, hollow discs 260 increasing in size (diameter) in the vertical direction (along the positive y-axis). The discs 260 are circular and form a tower shape symmetrical about the sensor central axis 299 (y-axis). The discs 260 are suspended in an interior passage 284 of the protection tube 250 via the heating element 218. Interior surfaces of the protection tube 250 are spaced away from outer surfaces of the discs 260 by a distance, where the distance decreases in the vertical direction. Thus, a disc nearest the inlet 210 has the smallest diameter and a disc nearest the outlet 214 has the largest diameter. The diameters of the discs 260 may incrementally increase along the vertical axis by a range of 10% to 50%. For example, a first disc directly above a second disc may have a diameter 25% larger than a diameter of the second disc, exposing an outer rim (edge) 262 of the first disc. An area of the interior passage 284 adjacent to the discs 260 decreases along the vertical axis. Outer rims 262, which face a direction of incoming exhaust flow in the interior passage 284, are flat surfaces exposed to and may come into contact with exhaust gas in the interior passage 284. An area of an exposed outer rim of the outer rims 262 may be based on a difference in adjacent discs of the discs 260. In this way, the area of the outer rims 262 may increase in the vertical direction. In another example, the outer rims 262 may be equal in area. In one example, the discs 260 may comprise a substantially uniform thickness. In another example, the discs 260 may be substantially uniform in volume, where a thickness of the discs 260 decreases corresponding to an increase in diameter in the vertical direction. By maintaining a uniform volume of the discs 260, the heating element 218 may consume less power in order to heat the sensor substrate 216. While there are eight of the discs 260 shown, other numbers of discs 260 may also be used.

First electrodes 220 are installed around an outer circumferential surface of each alternating disc of the discs 260 and second electrodes 222 are installed on an outer circumferential surface of each of the remaining discs of the discs 260. The outer circumferential surface is substantially parallel to exhaust flow in the interior passage 284. The outer rims 262 are located between the first 220 and second 222 electrodes. The discs 260 are positioned such that PM may be captured on the outer rims 262. PM captured along the outer rims 262 may bridge the first 220 and second 222 electrodes of adjacent discs, altering the measurement device 226 voltage (resistance) reading.

Incoming exhaust flow 298 refers to exhaust upstream of the PM sensor device 200, which may enter the inlet 210 of the protection tube 250 or flow around the protection tube 250. As such, the exhaust flow 298 is the exhaust gas that exits the PF. Larger particulates and water droplets 297 in the exhaust flow 298 may not enter the inlet 210 due to their greater momentum, compared to smaller particulates, carrying them past the inlet 210, thereby decreasing and/or preventing an amount of larger particulates being deposited onto the sensor element 216. Smaller PM in the exhaust gas may flow through the inlet 210 and enter the interior passage 284, where the exhaust gas may flow between the PM sensor element 254 and the interior surfaces of the protection tube 250. The interior passage 284 may have a circular cross-section. Exhaust gas in the interior passage 284 may contact one or more outer rims 262 of the discs 260, where smaller PM may be deposited. The exhaust gas traverses an entire height of the sensor substrate 216 before flowing through the outlet 214 and into the exhaust passage 280. Exhaust flowing out the outlet 214 may flow at an angle perpendicular to incoming exhaust flow 298 before merging with exhaust gas in the exhaust passage 280.

Accumulated PM on the outer rims 262 may be in contact with first 220 and second 222 electrodes simultaneously, thereby bridging (electrically coupling) the electrodes. In response to the bridging, the heating element 218 may be activated by the controller 12 in order to regenerate the sensor element 216. During regeneration, the PM is burned into ash, becoming readily available for exhaust gas to sweep the ash off the sensor element 216. Additionally or alternatively, the PF of the exhaust passage 280 may be determined degraded based on a time lapse between subsequent regenerations of the sensor element 216, as described below with respect to FIG. 5. Exhaust gas in the interior passage 284 flows through the outlet 214 and into the exhaust passage 280.

Thus, the PM sensor device includes a PM sensor element with a sensor substrate for capturing PM housing in a protection tube. The sensor substrate is a tower shape with a plurality of discs increasing in size along a vertical axis. The discs may have outer surfaces exposed to exhaust gas in protection tube, where the surfaces face a direction perpendicular to or opposite to exhaust flow in the tube. Circumferential surfaces face a direction perpendicular to exhaust flow and outer rims face a direction opposite exhaust flow. First electrodes are integrated onto circumferential surfaces of alternating discs and second electrodes are integrated onto circumferential surfaces of the remaining discs. The electrodes are separated from each other by the outer rims, where PM may accumulate. The PM may be electrically conductive and bridge the first and second electrodes, thereby altering a measured resistance of the electrodes and indicating a state of a PF in an exhaust passage upstream of the PM sensor.

FIG. 3 shows a schematic view of a second embodiment 300 of a PM sensor assembly (such as PM sensor assembly 200 of FIG. 2). As such, components previously introduced are numbered similarly in subsequent figures. The second embodiment 300 may function and be used as the PM sensor assembly 200 in the embodiment of FIG. 2. The electric components and protection tube are substantially similar and are not reintroduced for reasons of brevity. A PM sensor element 354 a sensor substrate 316, and discs 360 may be different in shape, but similar in function to PM sensor element 254, sensor substrate 216, and discs 260 shown in FIG. 2, respectively. The differences will be described below.

An axis system 390 comprising two axes, an x-axis in the horizontal direction and a y-axis in the vertical direction. A central axis 395 of an exhaust passage 380 is substantially parallel to the x-axis. A sensor central axis 399 is substantially parallel to the y-axis (perpendicular to the central axis 395). An incoming exhaust flow is depicted via arrows 298. Dashed arrows indicate a direction of exhaust flow in the protection tube 250.

The PM sensor element 354 comprises the sensor substrate 316 with a plurality of hollow discs 360 concentrically stacked adjacent to the inner surfaces of the protection tube 250. The discs 360 are symmetric about and spaced away from the sensor central axis 399. The discs 360 comprise a toroid (ring) cross-section along the x-axis with an inner diameter (opening) of the discs 360 decreasing up the vertical axis (y-axis). In this way, a size of the discs 360 increases while an area of an interior passage 284 decreases up the y-axis. A size of the discs may increase by a range of 10-50%. In one example, a first disc may be 25% bigger than a second disc directly below the first disc. First electrodes 220 are installed on inner circumferential surfaces of each alternating disc of the discs 360 while second electrodes 222 are installed on inner circumferential surfaces of the remaining discs of the discs 360. Inner rims 362 of the discs 360 are exposed along the interior passage 284 and separate the first electrodes 220 from the second electrodes 222. Exhaust gas flowing through the interior passage 284 (openings) between the discs 360 may deposit PM onto the inner rims 362 and bridge the first 220 and second 222 electrodes once the PM load exceeds threshold load. As described above, the PM sensor element 354 may be heated by the heating element 218 to burn off accumulated soot. The heating element 218 is physically coupled to and located between the inner surfaces of the protective tube 250 and the sensor substrate 316.

Thus, a PM sensor includes a protective tube and a sensor element located therein. The protective tube comprises an inlet oblique to a vertical axis of the tube, where the inlet faces a downstream direction relative to exhaust gas. The tube further comprises an outlet, located above the sensor element and facing a direction perpendicular to a direction of exhaust gas flow. The sensor element comprises a plurality of stacked, hollow discs, concentric with and symmetric about the vertical axis, increasing in size up the vertical axis. In one example, the discs are circular and spaced away from interior surfaces of the tube with an interior passage surrounding the discs. In another example, the discs are toroidal and in face-sharing contact with interior surfaces of the tube, and the interior passage runs through an opening of the discs. The openings of the discs decrease in diameter up the vertical axis. First electrodes are installed on outer surfaces of alternating discs of the discs and second electrodes are installed on outer surfaces of remaining discs of the discs. The first and second electrodes are spaced away from one another by outer rims of the discs. Particulate matter may accumulate onto the outer rims of the discs due to the inlet conducting a portion of exhaust gas from an exhaust passage up into the interior passage. If the accumulated particulate matter exceeds a threshold load, then the electrodes may become bridged. A heating element of the PM sensor may regenerate the sensor element in response to the bridging. A particulate filter of an exhaust passage may also be regenerated in response to the bridging, as will be described below.

FIG. 4 shows a schematic view of an example embodiment of a PM sensor assembly 400. The PM sensor assembly 400 may be used as PM sensor 162 of FIG. 1. The PM sensor assembly 400 comprises electrical components substantially identical to electrical components of the PM sensor assembly 200 of FIG. 2. Thus, similar components are numbered similarly and are not re-introduced for reasons of brevity. The PM sensor assembly 400 functions similarly to PM sensor assemblies 200 and 300 of FIGS. 2 and 3, respectively, but comprises a different structural motif as will be described herein.

An axes system 490 is shown comprising two axes, an x-axis in the horizontal direction and a y-axis in the vertical direction. A central axis 495 of the exhaust passage 480 is parallel to the x-axis. A sensor central axis 499 is parallel to the y-axis (perpendicular to the central axis 495). Arrows 498 indicate incoming exhaust flow flowing from a particulate filter (e.g., PF 72 of FIG. 1) to the PM sensor assembly 400 in the exhaust passage 480. Dashed arrows depict a direction of exhaust flow through the PM sensor assembly 400. Circles 497 indicate large particulates and water droplets.

PM sensor assembly 400 may include a cylindrical outer tube 450, fixed to an exhaust pipe 482, with a first opening 452, a second opening 454, and a third opening 456 located on an upstream side 408, a downstream side 406, and a bottom side 410, respectively. The first 452 and second 454 openings are parallel and aligned on a shared horizontal axis. The third opening 456 is located on a lower portion of the outer tube 450 and is perpendicular to the first 452 and second 454 openings. The sides are contiguous with one another and form the body of the cylindrical outer tube 450. The openings may be substantially identical in shape and size in some embodiments. The openings may be different in shape and/or size in other embodiments. In one example, the openings are elliptical, however, other shapes may be used without departing from the scope of this disclosure. The upstream side 452 is substantially normal to and facing the flow of incoming exhaust gases (arrow 498) in the exhaust passage 480. Thus, the upstream side 452 may be in direct contact with exhaust flow and exhaust gases exiting the PF (e.g., particulate filter 72 of FIG. 1) may flow in an unobstructed manner towards the upstream face 452. Further, no components may block or deflect the flow of exhaust gases from the PF to the PM sensor assembly 400. Thus, a portion of exhaust gases for sampling may be conducted via the first opening 452, which faces a direction of incoming exhaust flow, into an interior passage 484 of the outer tube 450. Thus, the first opening 452 may herein be referred to as inlet 452. The inlet 452 may uninterruptedly receive larger PM, water droplets, and smaller PM. Exhaust gas in the interior passage 484 may flow through the second opening 454 or inner flow tube 460, which is concentric with the outer tube 450 about the sensor central axis 499. An inner tube inlet 462 is vertically higher than the first 452, second 454, and third 456 openings. In this way, larger PM and water droplets may flow out the second opening 454 and into the exhaust passage 480 without flowing into the inner tube 460 due to their greater momentum compared to the smaller PM.

The inner tube 460 is hollow with an inner passage 466 aligned with the sensor central axis 499. The inlet 462 is proximal to a top surface 412 of the outer tube 450 and an outlet 464 is proximal to a hollow disc 472. The hollow disc 472 is circular and in face-sharing contact with inner surfaces of the outer tube 450 at a region of the outer tube 450 below the first 452 and second 454 openings. Thus, a diameter of hollow disc 472 is correspondingly less than a diameter of the outer tube 450. The hollow disc 472 may be impervious to exhaust flow in order to prevent exhaust from flowing directly from the interior passage 484, into a lower chamber 486, and out the third opening 456. Furthermore, the hollow disc 472 comprises a sensor substrate 470 along its center. The disc 472 and the sensor substrate 470 are concentric about the sensor central axis 499. In this way, the sensor substrate 470 aligns with the inner tube 460 such that exhaust gas flowing through the inner tube outlet 464 flows directly to the substrate 470 where PM may impinge upon surfaces of the substrate 470. A distance 476 between the inner tube outlet 464 and the sensor substrate 470 may be in a range of 30 to 50 micrometers, however, other distances may be used without departing from the scope of the disclosure. In one example, the distance 476 may be based on a size of larger particulates and/or water droplets, wherein the distance is less than the size of the larger particulates and/or water droplets. In this way, larger particulates and/or water droplets may not flow through the distance 476. The sensor substrate 470 may be ceramic with a porosity of less than 60%. A diameter of the sensor substrate 470 may be substantially equal to a diameter of the inner tube 460. The diameters may be unequal without departing from the scope of this disclosure. The first electrode 220, which is integrated into interior surfaces of the inner tube 460, may be bridged to the second electrode 222, which is integrated to a top surface of the sensor substrate 470. As described above, bridging the electrodes may alter a voltage measured by the measurement device 226 providing diagnostic information about a condition of the PF in the exhaust passage 480, as will be described in greater detail below. Additionally, the sensor substrate 470 may be regenerated in response to bridging the electrodes via a heating element 218, where the heating element forms a heating collar 474 around a top surface of the sensor substrate 470. Exhaust gas flowing out of the sensor substrate 470 flows into the lower chamber 486 and out through the third opening 456.

In another representation, a first example of the PM sensor assembly comprises concentric outer and inner tubes, where the outer tube is configured to receive and expel an exhaust gas sample and the inner tube is configured to conduct a portion of the exhaust gas sample toward a sensor substrate integrated in a hollow disc inside the outer tube. The first example of the PM sensor assembly further includes where a diameter of the inner tube and the sensor substrate are substantially equal and where the inner tube and the sensor substrate are aligned along a sensor central axis. The first example of the PM sensor further includes where the sensor substrate is spaced away from the inner tube along a y-axis in a downward direction. The first example of the PM sensor further includes a first electrode located along a bottom portion of the inner tube proximal to the sensor substrate and a second electrode located along a top portion of the sensor substrate proximal to the inner tube. The first example of the PM sensor further includes the first and second electrodes being electrically connected in response to a PM load exceeding a threshold PM load. The first example of the PM sensor further includes the inner tube and the sensor substrate are configured to receive exhaust gas and the sensor substrate is further configured to store PM in the exhaust gas. The first example of the PM sensor further includes a heating element annularly integrated around the sensor substrate, and where the heating element burns PM off the sensor substrate. The first example of the PM sensor further includes openings located along upstream, downstream, and bottom faces of the outer tube, and where the openings of each face are fluidly coupled to an exhaust passage.

Turning now to FIG. 5, a method 500 for determining a particulate load of a PM sensor assembly being greater than a threshold particulate load in order to regenerate the PM sensor is depicted. The method 500 may further depict degradation of a particulate filter in an exhaust passage is degraded based on a time interval between PM sensor regeneration being less than a threshold time interval.

Instructions for carrying out method 500 may be executed by a controller (e.g., controller 12 shown in FIG. 1) based on instructions stored on a memory of the controller and in conjunction with signals received from sensors of the engine system, such as the sensors described above with reference to FIGS. 1 and 2. The controller may employ engine actuators of the engine system to adjust engine operation, according to the methods described below.

Method 500 may be described in reference to components depicted in FIGS. 1, 2, 3, and 4. Specifically, the method 500 may be described with the controller 12, the PF 72, the exhaust gas sensor 162, the PM sensor assembly 200, 300, and 400, the first and second electrodes 220 and 222, the heating element 218, and the electric circuit 258 with reference to FIGS. 1, 2, 3, and 4.

Method 500 being at 502 to determine, estimate, and/or measure current engine operating parameters. Current engine operating parameters may include but are not limited to engine load, engine speed, vehicle speed, manifold vacuum, throttle position, exhaust pressure, and an air/fuel ratio.

At 504, the method 500 includes measuring an electrical resistance of the first and second electrodes. In the embodiment of FIG. 5, the first electrode may have a greater resistance than the second electrode. However, it will be appreciated by someone skilled in the art that the second electrode may have a greater resistance than the first electrode.

At 506, the method 500 includes determining if the electrodes are electrically connected (e.g., bridged). The electrodes may become bridged as soot is deposited onto outer surfaces of the sensor substrate between the electrodes. As described above, soot may deposit onto outer rims (outer rims 262 of FIG. 2) and connect the electrodes. Additionally, soot may deposit onto a top surface of a sensor substrate (sensor substrate 470) between the sensor substrate and an inner tube (inner tube 460). As the soot builds up between the first and second electrodes, the soot may touch both electrodes simultaneously and as a result, the electrodes are bridged. When the electrodes are bridged, the resistance of the first electrode may decrease to a resistance of the second electrode due to the conductivity of the soot. If the resistance of the first electrode is greater than the resistance of the second electrode, then the electrodes are not bridged and the method 500 proceeds to 508 to maintain current engine operating parameters and to not regenerate the PM sensor in the PM assembly. Furthermore, a particulate filter (PF) in an exhaust passage may not be leaking or fully loaded with PM (e.g., a PF PM load is less than a threshold PF PM load). Thus, the PF in the exhaust passage may not be regenerated.

If the resistance of the first electrode is substantially equal to the resistance of the second electrode, then the electrodes are bridged and the method 500 proceeds to 510 to activate an electric circuit of the PM sensor in order to regenerate the PM sensor. The electric circuit may be electrically connected to one or more of the first and second electrodes. Thus, the heating element may be activated by one or more of the first and second electrodes in response to the first and second electrodes being bridged. Alternatively, the heating element may be activated (e.g., switched on) via the controller in response to determining that the first and second electrodes are bridged. The controller may further adjust actuators of the engine in response to activating the electric circuit. For example, the controller may adjust an engine operation in order to regenerate the particulate filter located in the exhaust passage. The adjustments may include retarding spark, decreasing an air/fuel ratio of one or more cylinders, increasing the air/fuel ratio of one or more cylinders, and/or increasing a post-injection volume. In this way, regeneration of the PM sensor of the PM sensor assembly may trigger a regeneration of the PF located in the exhaust passage based on the first and second electrodes being bridged.

At 512, the method 500 includes disabling the PM sensor regeneration in response to the first and second electrodes no longer being bridged. The first and second electrodes may no longer be bridged after the heating element regenerates the PM sensor and thus, burns off at least a portion of accumulated soot on the PM sensor. By burning off the soot, the bridge between the first and second electrodes may also be burned and the resistance of the first electrode may become greater than the resistance of the second electrode. The controller may deactivate the electric circuit in response to determining the resistance of the first electrode is greater than the resistance of the second electrode. Alternatively, the first and second electrodes may be electrically coupled to the electric circuit and the circuit may be deactivated by the first and second electrodes in response to the electrodes no longer being bridged.

The regeneration of the PF in the exhaust passage may also be terminated in response to deactivating the heating element. The controller may adjust engine operation back to an optimal engine operation based on a current engine load. Thus, a duration of regeneration for the PM sensor and the PF are substantially equal. Additionally or alternatively, the regeneration of the PF in the exhaust passage may be terminated after a threshold duration has passed after termination of the heating element. For example, the heating element is deactivated and then after the threshold duration has passed, the controller signals actuators of the engine to return to a nominal operation in order to deactivate PF regeneration.

In one example, additionally or alternatively, the regeneration of the PF sensor and the regeneration of the PF may operate for lengths of a first threshold and a second threshold, respectively. In this way, lengths of regeneration of the PF sensor and the PF may be independent. In other words, the first threshold may not be equal to the second threshold. In one embodiment, the first threshold may be less than the second threshold (e.g., the PF is regenerated for a greater length of time compared to the PM sensor). In another embodiment, the first threshold may be greater than the second threshold (e.g., the PF sensor is regenerated for a greater amount of time than the PF).

At 514, the method includes determining a time interval between a last regeneration and a current regeneration of the PM sensor. The last regeneration is defined as a regeneration event that occurred directly before a current regeneration event. The time interval may be calculated based on a duration of time between initiation of the last regeneration and initiation of the current regeneration (e.g., 120 minutes). A time interval may be less than a previous time interval as the PF in the exhaust passage (e.g., particulate filter 72 of FIG. 1) becomes degraded and captures less soot. For example, the particulate filter develops leaks (e.g., cracks), which may allow a greater amount of soot to flow to the PF sensor, resulting in more frequent regenerations of the PF sensor.

At 516, the method 500 determines if the measured time interval is less than a threshold time interval. The threshold time interval may be based on a set threshold (e.g., 200 minutes), a last time interval measured, or a percentage of the last time interval measured (e.g., 50% of the last time interval). Further, the threshold time interval may be based on a threshold that indicates that the time interval is decreasing and the PF sensor has to be regenerated at an increasing rate. Additionally or alternatively, the threshold time interval may be adjusted based on engine operating parameters. For example, the threshold time interval may be decreased as an engine load increases.

If the time interval is not less than the threshold time interval, then the method 500 proceeds to 508 to maintain current engine operation and continue monitoring the electrodes of the PM sensor.

If the time interval is less than the threshold time interval, then the method 500 proceeds to 518 to indicate the PF of the exhaust passage, upstream of the PM sensor assembly, is leaking. Indication of the PF leaking includes adjusting an engine operation and activating an indicator lamp 520 (e.g., in order to indicate to a vehicle operator that the PF is degraded and needs to be replaced).

As an example, a controller (e.g., controller 12) may signal various actuators of an engine (e.g., throttle 62 of engine 10) to limit a torque output of the engine in order to reduce exhaust produced to meet emissions standards. As another example, additionally or alternatively, the method 500 may advance one or more of a spark timing and fuel injection, increase air/fuel ratio, and/or increase EGR. By increasing EGR flow to one or more cylinders of the engine, a combustion mixture temperature(s) is decreased and a volume of fuel injection may be decreased. By doing this, an amount of soot being exhausted from one or more cylinders of the engine may be decreased.

Thus, the method of FIG. 5 provides a method comprising diverting exhaust gas from an exhaust pipe to a PM sensor assembly, where the PM sensor assembly includes a PM sensor with electrodes on a downstream surface and an electric circuit on an upstream surface. The method includes adjusting engine operation based on electrodes of the PM sensor being bridged (e.g., connected). The bridging is based on resistances of the electrodes becoming substantially equal.

In this way, a PM sensor assembly may receive a sample exhaust flow from an exhaust passage in order to determine a PM load of a PF in the exhaust passage. PM from the exhaust accumulates onto a surface of a PM sensor located within the PM sensor assembly in order to signal a regeneration and/or degradation of the PF. The technical effect of using a protection tube is to prevent larger particulates and/or water droplets from impinging onto surfaces of a sensor substrate so that the PM sensor may provide accurate diagnostic information regarding a status of the PF in the exhaust passage. By doing this, an accuracy of a determination of a PF being fully loaded and/or degraded is increased.

A system comprising a plurality of hollow discs increasing in size along a vertical axis, a first electrode installed on surfaces of each alternating disc of the plurality of discs, a second electrode installed on surfaces of each remaining disc of the plurality of discs, and a tube with an inlet facing a downstream direction relative to engine exhaust flow. A first example of the system further includes the discs increase in diameter up the vertical axis. A second example of the system optionally including the first example further includes where the discs are spaced away from an interior of the tube with an interior passage located therein. A third example of the system optionally including the first and/or second examples further includes where the discs are circular, the system further comprising a sensor output coupled with the electrodes. A fourth example of the system includes one or more of the first through third examples further includes the discs are in face-sharing contact with an interior of the tube, and an interior passage extends through openings of the discs. A fifth example of the system optionally includes one or more of the first through fourth examples further includes where the discs are toroidal and the openings decrease in diameter up the vertical axis, the system further comprising a sensor output coupled with the electrodes. A sixth example of the system optionally includes one or more of the first through fifth examples further includes where the discs comprise outer rims located between the first and second electrodes, the outer rims configured to capture particulate matter in the exhaust flow. A seventh example of the system optionally includes one or more of the first through sixth examples further including where a heating element integrated into the discs, where the heating element is structured to burn off accumulated particulate matter stored onto the discs. An eighth example of the system optionally includes one or more of the first through seventh examples further including where the tube is cylindrical and comprises an outlet located above the discs, and where the outlet faces a direction perpendicular to exhaust gas flow. A ninth example of the system optionally includes one or more of the first through eighth examples further including where the tube comprises an interior passage for conducting exhaust gas flow, and where the interior passage decreases in size up the vertical axis.

A method comprising directing a portion of exhaust gas into a protective tube through an oblique opening on a bottom of the tube, flowing the portion of exhaust gas through an interior passage of the protective tube in contact with surfaces of a plurality of concentrically stacked, hollow discs, and accumulating particulate matter from the portion of exhaust gas onto the surfaces of the discs. A first example of the method further including generating a sensor output signal indicative of particulate matter in the exhaust gas, wherein accumulating particulate matter beyond a threshold load bridges first and second electrodes integrated into alternating hollow discs. A second example of the method optionally including the first example further includes the bridging the first and second electrodes signals a regeneration of the hollow discs.

A system comprising a sensor tube positioned in a highest point of an engine exhaust passage, a plurality of concentrically stacked, hollow discs increasing in width up a vertical axis of the tube and having a first electrode installed on outer surfaces of alternating discs of the plurality of discs and a second electrode installed on outer surfaces remaining discs of the plurality of discs, outer rims of the plurality of discs located between the first and second electrodes. A first example of the system further includes where the tube comprises an inlet oblique to the vertical axis facing a downstream direction relative to a direction of exhaust gas flow and configured to conduct a portion of exhaust gas up into an interior passage of the tube. A second example of the system optionally including the first example further includes where the discs are positioned such that a portion of particulate matter in the portion of exhaust gas accumulates onto the outer rims and outer surfaces of the discs. A third example of the system optionally including one or more of the first and second examples further includes where an interior passage of the tube surrounds the discs. A fourth example of the system optionally includes one or more of the first through third examples further includes where the discs surround a portion of an interior passage of the tube. A fifth example of the system optionally includes one or more of the first through fourth examples further includes where the first and second electrodes are electrically coupled in response to a particulate matter load exceeding a threshold load. A sixth example of the system optionally includes one or more of the first through fifth examples further includes where the hollow discs are symmetric about the vertical axis of the tube.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A system comprising:
a tube having a plurality of hollow discs increasing in size along a vertical axis of the tube, a first electrode installed on surfaces of each alternating disc of the discs, a second electrode installed on surfaces of each remaining disc of the discs, where an inlet of the tube faces a downstream direction relative to engine exhaust flow, the axis of the tube being perpendicular to a direction of exhaust flow.

2. The system of claim 1, wherein the discs increase in diameter up the vertical axis.

3. The system of claim 1, wherein the discs are spaced away from an interior of the tube with an interior passage located therein.

4. The system of claim 3, wherein the discs are circular, the system further comprising a sensor output coupled with the electrodes.

5. The system of claim 1, wherein the discs are in face-sharing contact with an interior of the tube, and an interior passage extends through openings of the discs.

6. The system of claim 5, wherein the discs are toroidal and the openings decrease in diameter up the vertical axis, the system further comprising a sensor output coupled with the electrodes.

7. The system of claim 1, wherein the discs comprise outer rims located between the first and second electrodes, the outer rims configured to capture particulate matter in the exhaust flow.

8. The system of claim 1, further comprising a heating element integrated into the discs, where the heating element is structured to burn off accumulated particulate matter stored onto the discs.

9. The system of claim 1, wherein the tube is cylindrical and comprises an outlet located above the discs, and where the outlet faces a direction perpendicular to exhaust gas flow.

10. The system of claim 1, wherein the tube comprises an interior passage for conducting exhaust gas flow, and where the interior passage decreases in size up the vertical axis.

11. A method comprising:
directing a portion of exhaust gas into a protective tube through an oblique opening on a bottom of the tube;
flowing the portion of exhaust gas through an interior passage of the protective tube in contact with surfaces of a plurality of concentrically stacked, hollow discs, the discs' diameter increasing up a vertical tube axis; and
accumulating particulate matter from the portion of exhaust gas onto the surfaces of the discs.

12. The method of claim 11, further comprising generating a sensor output signal indicative of particulate matter in the portion of exhaust gas, wherein accumulating particulate matter beyond a threshold load bridges first and second electrodes integrated into alternating hollow discs.

13. The method of claim 12, wherein the bridging the first and second electrodes signals a regeneration of the hollow discs.

14. A system comprising:
a sensor tube positioned in a highest point of an engine exhaust passage; and
a plurality of concentrically stacked, hollow discs increasing in width up a vertical axis of the tube and having a first electrode installed on outer surfaces of alternating discs of the plurality of discs and a second electrode installed on outer surfaces of remaining discs of the plurality of discs,
wherein outer rims of the plurality of discs are located between the first and second electrodes.

15. The system of claim 14, wherein the tube comprises an inlet oblique to the vertical axis facing a downstream direction relative to a direction of exhaust gas flow and configured to conduct a portion of exhaust gas up into an interior passage of the tube.

16. The system of claim 15, wherein the discs are positioned such that a portion of particulate matter in the portion of exhaust gas accumulates onto the outer rims and outer surfaces of the discs.

17. The system of claim 14, wherein an interior passage of the tube surrounds the discs.

18. The system of claim 14, wherein the discs surround a portion of an interior passage of the tube.

19. The system of claim 14, wherein the first and second electrodes are electrically coupled in response to a particulate matter load exceeding a threshold load.

20. The system of claim 14, wherein the hollow discs are symmetric about the vertical axis of the tube.

* * * * *